US012741077B2

(12) United States Patent
Kibbel et al.

(10) Patent No.: US 12,741,077 B2
(45) Date of Patent: Sep. 22, 2026

(54) METHOD FOR OPERATING AN OPHTHALMIC SURGICAL SYSTEM, AND OPHTHALMIC SURGICAL SYSTEM

(71) Applicant: Carl Zeiss Meditec AG, Jena (DE)

(72) Inventors: Steffen Kibbel, Lauchheim (DE); Christoph Kuebler, Oberkochen (DE); Susanne Kohlhammer, Blaustein (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/612,838

(22) Filed: Mar. 21, 2024

(65) Prior Publication Data

US 2024/0226410 A1 Jul. 11, 2024

Related U.S. Application Data

(63) Continuation of application No. PCT/EP2022/075853, filed on Sep. 16, 2022.

(30) Foreign Application Priority Data

Sep. 21, 2021 (DE) ..................... 10 2021 124 405.6

(51) Int. Cl.
*A61M 1/00* (2006.01)

(52) U.S. Cl.
CPC ........... *A61M 1/77* (2021.05); *A61M 2205/14* (2013.01); *A61M 2210/0612* (2013.01)

(58) Field of Classification Search
CPC ... A61F 9/00745; A61F 9/00736; A61F 9/007
See application file for complete search history.

(56) References Cited

U.S. PATENT DOCUMENTS 4,465,470 A * 8/1984 Kelman .............. A61F 9/00736 604/27
6,398,754 B1 * 6/2002 Sutton ................ A61F 9/00745 604/35

(Continued)

FOREIGN PATENT DOCUMENTS

DE 10 2016 201 297 B3 3/2017
DE 10 2017 218 632 A1 4/2019

(Continued)

OTHER PUBLICATIONS

International Search Report of the European Patent Office dated Jan. 9, 2023 for international application PCT/EP2022/075853 on which this application is based.

(Continued)

*Primary Examiner* — Scott J Medway
(74) *Attorney, Agent, or Firm* — Walter Ottesen, P.A.

(57) ABSTRACT

First fluid lines for fluidically coupling a console to a medical instrument are connected to the console. The first fluid lines include a first irrigation line and a first aspiration line. Instrument-side ends of the first fluid lines are fluidically coupled to one another. A treatment fluid is conveyed through the first fluid lines from a source to a collecting container via a console-side pump. A second fluid line for the fluid is connected on the console side for fluidically coupling the console to the medical instrument or a further medical instrument. An instrument-side end of the second fluid line is fluidically coupled to at least one of the instrument-side ends of the first fluid lines. The fluid is conveyed through the second fluid line via the pump. A connection of the second fluid line is detected and the fluid is automatically applied to the second fluid line thereupon.

9 Claims, 5 Drawing Sheets

(56) References Cited

U.S. PATENT DOCUMENTS

| | | | | |
|---|---|---|---|---|
| 10,821,222 | B2 * | 11/2020 | Pananen | G01V 15/00 |
| 2007/0239102 | A1 | 10/2007 | Bourne | |
| 2008/0154095 | A1 * | 6/2008 | Stubkjaer | A61M 3/0216 600/156 |
| 2010/0125257 | A1 | 5/2010 | Perkins et al. | |
| 2011/0295193 | A1 * | 12/2011 | Fitzgerald | A61F 9/00736 604/22 |
| 2012/0172849 | A1 * | 7/2012 | Skinner | A61F 9/00736 700/282 |
| 2017/0059376 | A1 * | 3/2017 | Bochenko | A61M 5/172 |
| 2017/0216093 | A1 | 8/2017 | Kuebler et al. | |
| 2017/0224888 | A1 * | 8/2017 | Hickey | A61M 3/0208 |
| 2020/0100851 | A1 | 4/2020 | Marcuk | |
| 2022/0133537 | A1 * | 5/2022 | Govari | A61F 9/00736 606/107 |
| 2023/0346594 | A1 * | 11/2023 | Gurskis | A61F 7/12 |

FOREIGN PATENT DOCUMENTS

| | | | | |
|---|---|---|---|---|
| DE | 102018130376 | A1 * | 6/2020 | A61F 9/00736 |
| WO | 2010/056972 | A1 | 5/2010 | |
| WO | WO-2019076411 | A1 * | 4/2019 | |

OTHER PUBLICATIONS

English translation and International Preliminary Report on Patentability from The International Bureau of WIPO dated Mar. 26, 2024 for international application PCT/EP2022/075853 on which this application is based.

English translation and Written Opinion of the International Searching Authority dated Jan. 9, 2023 for international application PCT/EP2022/075853 on which this application is based.

Partial English translation and Office action of the Japanese Patent Office dated Mar. 11, 2025 for corresponding Japanese patent application 2024-517462.

* cited by examiner 36
52
46
49
45
3
2
43
56
44
47
41
40
37
53
38
39
54
1
55
48
50
35
42
20
51

METHOD FOR OPERATING AN OPHTHALMIC SURGICAL SYSTEM, AND OPHTHALMIC SURGICAL SYSTEM

CROSS-REFERENCE TO RELATED APPLICATIONS

This application is a continuation application of international patent application PCT/EP2022/075853, filed Sep. 16, 2022, designating the United States and claiming priority from German application 10 2021 124 405.6, filed Sep. 21, 2021, and the entire content of both applications is incorporated herein by reference.

TECHNICAL FIELD

The disclosure relates to a method for operating an ophthalmic surgical system, wherein at least two first fluid lines for fluidically coupling a console of the ophthalmic surgical system to at least one medical treatment instrument of the ophthalmic surgical system are connected to the console, with the at least two first fluid lines including at least one first irrigation line and at least one first aspiration line, treatment instrument-side ends of the at least two first fluid lines are fluidically coupled to one another, and a treatment fluid is conveyed through the at least two first fluid lines from a treatment fluid source to a collecting container of the ophthalmic surgical system via a console-side pumping apparatus. The disclosure also relates to an ophthalmic surgical system for treating an eye, at least having at least one medical treatment instrument for treating the eye, a console for controlling the at least one medical treatment instrument at least during an intended operation, at least two first fluid lines for fluidically coupling the console to the at least one medical treatment instrument, with the at least two first fluid lines being connectable to the console and to the at least one medical treatment instrument, with the at least two first fluid lines including at least one first irrigation line and at least one first aspiration line, wherein the ophthalmic surgical system is configured to fluidically couple treatment instrument-side ends of the at least two first fluid lines to one another in the console connected state and convey a treatment fluid through the at least two first fluid lines from a treatment fluid source to a collecting container of the ophthalmic surgical system via a console-side pumping apparatus.

BACKGROUND

Ophthalmic surgical systems, consoles therefor, and also medical treatment instruments, in particular handpieces, and methods therefor are known in the prior art, and so in principle there is no need for any separate documentary evidence in this respect. Various surgical techniques are known for example for the treatment of a clouding of the crystalline lens, also known in medicine as a cataract. The most widespread technique is phacoemulsification, in which a thin hollow needle of a handpiece is introduced into a capsular bag, in which the crystalline lens is arranged, and is induced to make ultrasonic vibrations. The lens can be emulsified via the vibrating hollow needle, and lens particles released in the process can be aspirated through an aspiration line via a pump. In the process, an irrigation fluid or treatment fluid is supplied. The lens particles are aspirated, together with this fluid, as aspiration fluid. As soon as the lens has been completely emulsified and removed, a new artificial lens can be inserted into the then empty capsular bag. The treated patient can in this way recover good vision.

An advanced ophthalmic surgical system that has proven particularly suitable for phacoemulsification is disclosed in US 2017/0216093, for example. In this system, two fluid pumps of a pumping apparatus fluidically connected in parallel are used in each case for the irrigation and also for the aspiration. Each of the fluid pumps has a pump chamber, and a drive chamber separated from the pump chamber via a movably arranged partition element. For example, the partition element may have an elastic configuration and be securely clamped, or else it can be displaceably arranged between the chambers. For the operation as intended of the fluid pump, the drive chamber is acted upon by a drive fluid whose drive pressure is varied for performing a respective pump stroke. Depending on this, a deflection position of the partition element thus changes, which has a corresponding effect on the pump chamber. The pump chamber is acted upon by the respective treatment fluid, for example the irrigation fluid, the aspiration fluid or the like. The delivery action can then be achieved by suitably controlling a respective inlet valve and a respective outlet valve of the fluid pump.

A deflection position of the partition element is detected via a deflection position sensor assigned to the respective fluid pump. A control device of the ophthalmic surgical system, in particular of the console, controls the function of the fluid pump at least on the basis of a sensor signal of the deflection position sensor and of a drive pressure signal supplied via a drive pressure sensor. In addition, the control device can, for example, control the inlet valve and the outlet valve.

By alternate actuation of the respective two fluid pumps connected in parallel, a volumetric flow with very little fluctuation can be obtained during a surgical procedure. In this way, an almost constant intraocular pressure can be obtained in the capsular bag. As long as sufficient irrigation fluid can be delivered, the system can be operated almost without interruption of the flow of irrigation fluid, even during a very protracted surgical procedure.

Starting from a non-use situation, provision is frequently made for the treatment fluid to be applied to the at least two first fluid lines for the purpose of putting the ophthalmic surgical system into use before an ophthalmic surgical treatment is performed. By preference, the treatment fluid should be applied to substantially the entirety of the fluid lines. To this end, the fluid lines are connected to the console, and treatment instrument-side ends of the at least two first fluid lines are fluidically coupled. Thereupon, the generally console-side pumping apparatus is used to convey the treatment fluid through the at least two first fluid lines, with the result that these are filled or rinsed, preferably in full, via the treatment fluid. The treatment instrument-side ends are then fluidically decoupled and the ends are coupled to the medical treatment instrument in particular so that the medical treatment can be started.

The aforementioned put-into-operation process needs to be carried out again, manually as a rule, should the medical treatment instrument be changed during the medical treatment or should a further medical treatment instrument be put into use. This is time-consuming and, under certain circumstances, obstructive during a medical treatment—such as a surgical procedure on the eye.

SUMMARY

It is an object of the disclosure to provide an improved method for operating an ophthalmic surgical system and an ophthalmic surgical system in relation to putting medical treatment instruments into operation.

The aforementioned object is, for example, achieved via a method for operating an ophthalmic surgical system, wherein at least two first fluid lines for fluidically coupling a console of the ophthalmic surgical system to at least one medical treatment instrument of the ophthalmic surgical system are connected to the console, with the at least two first fluid lines including at least one first irrigation line and at least one first aspiration line; treatment instrument-side ends of the at least two first fluid lines are fluidically coupled to one another; a treatment fluid is conveyed through the at least two first fluid lines from a treatment fluid source to a collecting container of the ophthalmic surgical system via a console-side pumping apparatus; at least one second fluid line for the treatment fluid is connected on the console side for fluidically coupling the console to the at least one medical treatment instrument or a further medical treatment instrument; a treatment instrument-side end of the at least one second fluid line is fluidically coupled to at least one of the treatment instrument-side ends of the at least two first fluid lines; the treatment fluid is conveyed through the at least one second fluid line via the console-side pumping apparatus. The method includes: detecting a connection of the at least one second fluid line; and, automatically applying the treatment fluid to the at least one second fluid line upon connection to the console.

The aforementioned object is, for example, also achieved via an ophthalmic surgical system for treating an eye. The ophthalmic surgical system includes: at least one medical treatment instrument for treating the eye; a console for controlling the at least one medical treatment instrument; at least two first fluid lines for fluidically coupling the console to the at least one medical treatment instrument; the at least two first fluid lines being connectable to the console and to the at least one medical treatment instrument; the at least two first fluid lines including at least one first irrigation line and at least one first aspiration line; wherein the ophthalmic surgical system is configured to fluidically couple treatment instrument-side ends of the at least two first fluid lines to one another in a console connected state and convey a treatment fluid through the at least two first fluid lines from a treatment fluid source to a collecting container of the ophthalmic surgical system via a console-side pumping apparatus; at least one second fluid line for the treatment fluid configured to fluidically couple the console to the at least one medical treatment instrument or a further medical treatment instrument;

wherein the ophthalmic surgical system is configured to fluidically couple a treatment instrument-side end of the at least one second fluid line to at least one of the treatment instrument-side ends of the at least two first fluid lines and convey the treatment fluid through the at least one second fluid line via the console-side pumping apparatus; and, the ophthalmic surgical system being configured to detect a connection of the at least one second fluid line and automatically apply the treatment fluid to the at least one second fluid line upon connection to the console.

In relation to a generic method, the disclosure proposes in particular that at least one second fluid line for the treatment fluid is connected on the console side for fluidically coupling the console to the at least one medical treatment instrument or a further medical treatment instrument, a treatment instrument-side end of the at least one second fluid line is fluidically coupled to at least one of the treatment instrument-side ends of the at least two first fluid lines, and the treatment fluid is conveyed through the at least one second fluid line via the console-side pumping apparatus.

In relation to a generic ophthalmic surgical system, the disclosure proposes in particular that the ophthalmic surgical system includes at least one second fluid line for the treatment fluid which is provided to fluidically couple the console to the at least one medical treatment instrument or a further medical treatment instrument, wherein the ophthalmic surgical system is configured to fluidically couple a treatment instrument-side end of the at least one second fluid line to at least one of the treatment instrument-side ends of the at least two first fluid lines and convey the treatment fluid through the at least one second fluid line via the console-side pumping apparatus.

The disclosure is based inter alia on the idea of better assisting the user of the ophthalmic surgical system during the intended use, for example with a medical treatment on the eye. The disclosure can provide significant assistance to the user or surgeon, especially if the medical treatment instrument should be changed or a further medical treatment instrument should be put into operation during the intended use or a surgical procedure on the eye. For example, if the additional use of a second fluid line becomes necessary, for example when a further medical treatment instrument is put into operation, then the treatment fluid must also be applied to the at least one second fluid line before the further medical treatment instrument can be used. If the treatment fluid is a treatment liquid, for example an irrigation liquid or the like, then the fluid lines should preferably not contain any gas or air bubbles. As a result, complete and reliable functionality can already be realized at the outset of use of the medical treatment instrument. Such a procedure is also referred to as priming.

During a surgical procedure, it was found to be disadvantageous for the user or surgeon if the priming interrupts the surgical procedure, especially since the priming that serves to put a handpiece into use within the scope of an ophthalmic surgical procedure may take several seconds and up to 1.5 minutes. This can be avoided as a result of the disclosure.

For example, the medical treatment instrument can be a handpiece for an ophthalmic surgical treatment, within the scope of which a crystalline lens of an eye should be removed. However, this may moreover also relate to a handpiece suitable for a posterior segment surgical procedure on the eye, a vitrectomy cutter or the like. As a rule, such medical treatment instruments are connected to the console via at least one aspiration line or at least one irrigation line, which are generally in the form of tubing.

These lines and also elements or units of the console to which treatment fluid is applied are rinsed, at least before the intended use and/or optionally also while a surgical procedure is performed. This can be achieved within the scope of the procedure according to the disclosure. In this context, provision is generally made for treatment instrument-side ends of the at least two first fluid lines to be fluidically coupled to one another. This can be implemented by suitably connecting the treatment instrument-side ends of the first fluid lines by virtue of these being coupled directly or via a fluidic coupling element. In principle, this may also be realized by the medical treatment instrument itself under certain circumstances, by virtue of the medical treatment instrument being configured to provide an appropriate, preferably controllable, fluidic connection, for example by virtue of an appropriate coupling function of the medical treatment instrument being activated or the like.

For this purpose, and also for the purpose of the intended use, the ophthalmic surgical system includes a treatment fluid source which may be arranged for example on the console side on an appropriate holder. The treatment fluid source may provide the treatment fluid, which can for example be the irrigation fluid, in particular an irrigation liquid. The treatment fluid is conveyed through the irrigation line from the console to the treatment instrument-side end of the irrigation line. The fluidic coupling to the aspiration line at the treatment instrument-side end results in the treatment fluid subsequently being conveyed through the aspiration line and back to the console, where it is supplied to a collecting container. For example, the collecting container can be a receptacle in which the treatment fluid conveyed on the console side by the aspiration line is stored.

According to the disclosure, provision is made on the console side for at least one second fluid line for the treatment fluid to be connected for fluidically coupling the console to the at least one medical treatment instrument or a further medical treatment instrument. For example, this fluid line can be an irrigation line or else an aspiration line.

Moreover, it is naturally also possible to provide a plurality of fluid lines which can be irrigation lines and/or aspiration lines, depending on requirements. So as to be able to realize the desired rinsing procedure, the at least one second fluid line is also envisaged as having its treatment instrument-side end fluidically coupled to at least one of the treatment instrument-side ends of the at least two first fluid lines. This provides the option of conveying treatment fluid through the at least one second fluid line as well. Accordingly, the console-side pumping device is configured to apply the treatment fluid to the second fluid line.

The parts or elements or units of the console to which treatment fluid is applied are frequently arranged together in a separate, interchangeable part, which is generally configured as a cartridge. As a result, the console itself need not come into direct contact with the treatment fluid. The cartridge is an interchangeable part which is configured as a single use part, in particular a disposable part, as a rule. This makes it possible to easily achieve a good stability for the intended use. Thus, the cartridge inter alia also includes elements of the pumping apparatus which come into direct contact with the treatment fluid. For example, the pumping apparatus includes at least one fluid pump for each of irrigation and aspiration, the pump preferably being included in its entirety in the cartridge. For example, a drive for the fluid pump may be provided on the console side such that, where possible, the cartridge includes only elements that come into direct contact with the treatment fluid.

Moreover, the cartridge may also include valve elements that can be used to control the functions relating to conveying the treatment fluid and also guiding the treatment fluid to the respective fluid lines. In this case, too, provision can be made for appropriate valve drives to be provided for on the console side. With the cartridge, therefore, a replacement part or disposable part can be made available which can serve to ensure the sterility of the ophthalmic surgical system for a respective surgical procedure on the eye, particularly as regards the treatment fluid. This is because the treatment fluid only needs to be fed through the cartridge, and so the treatment fluid need not flow through the console and also need not come into contact with the console. In this way, after a respective use of the ophthalmic surgical system, it is easily possible to restore the sterility of the ophthalmic surgical system at any time by replacing the cartridge in the console. The cartridge may have a cartridge housing, which may be formed from a suitable material, for example a plastic or the like. The fluid pumps may at least in part, be configured in one piece with the cartridge housing.

Moreover, a connection of the at least one second fluid line is detected, and the treatment fluid is automatically applied to the at least one second fluid line upon connection to the console. As a result of this, it is not necessary for the user of the ophthalmic surgical system to carry out any further actions in order to rinse or prime the at least one second fluid line.

It is also proposed that the treatment fluid is applied to the fluid lines in one method step, in particular for putting the ophthalmic surgical system into use. By preference, the treatment fluid is essentially applied approximately simultaneously to the fluid lines, with the result that the fluid lines preferably only contain the treatment fluid at the end of this method step.

It is also proposed that the treatment fluid is applied to the at least one second fluid line during an intended use of the at least one medical treatment instrument. As a result, the at least one second fluid line can also be rinsed during the intended use, for example when performing a surgical procedure on the eye. This is particularly advantageous if a further medical treatment instrument which is fluidically coupled to the at least one second fluid line is used during the performance of the surgical procedure on the eye. Thus, the user of the ophthalmic surgical system substantially need not interrupt their treatment or performance of the surgical procedure on the eye.

One development proposes that the at least one second fluid line is a second aspiration line for fluidically coupling the further medical treatment instrument. Moreover, however, it is also possible to provide a second irrigation line for the further medical treatment instrument. Thoughts in this respect are applicable accordingly. For example, the further medical treatment instrument can be a further handpiece. As a result of the at least one second aspiration line, the further medical treatment instrument can for example be used on the same eye at the same time as the first medical treatment instrument. In principle, there is no need to provide a second irrigation line for the further medical treatment instrument in such a case. With particular advantage, the at least one first aspiration line and the at least one second aspiration line can be fluidically coupled to the same fluid pump of the pumping apparatus.

It is also proposed that the console activates the fluid lines individually via a valve apparatus. As a result, the respective fluid line for the respective medical treatment instrument can be activated or deactivated according to requirements. To this end, the valve apparatus may include one or more suitable valves which can be controlled console-side by the control device.

One development proposes that for at least one of the fluid lines, a fluid resistance is ascertained in relation to the conveyance of the treatment fluid through this fluid line. For example, the fluid resistance can be measured via sensors provided on the console side. To this end, the function of the respective fluid pump, for example, can also be taken into account. A function of the ophthalmic surgical system can be monitored using the fluid resistance.

Moreover, it is proposed that at least one operational parameter of the ophthalmic surgical system is set on the basis of the ascertained fluid resistance. For example, the operational parameter can relate to the pumping function of the at least one fluid pump of the pumping apparatus in the console, or else to a valve setting of the valve device and/or the like. However, it is also possible to generate alerts or operational notifications, for example, which can be output console side via the control device, for example within the scope of a display for the user, an audio output for the user and/or the like.

It is also proposed that the medical treatment instrument connected to the respective fluid line is determined at least on the basis of the ascertained fluid resistance, with at least one operational parameter of the determined medical treatment instrument being set, in particular on the basis of the determined medical treatment instrument. For example, it is possible to ascertain whether the medical treatment instrument is a vitrectomy cutter, an ultrasonic handpiece or the like. It is then possible, on the basis of the ascertained or determined medical treatment instrument, to ascertain the functions for the intended operation and set corresponding operational parameters console side, with the result that the adjustment outlay for the user can be reduced, and might even be able to be avoided in its entirety. Moreover, the reliability can be improved because this allows automatic recognition of the medical treatment instrument.

The advantages and effects indicated for the method according to the disclosure are also equally applicable to the ophthalmic surgical system, and vice versa. In particular, method features may therefore also be formulated as device features, and vice versa.

BRIEF DESCRIPTION OF DRAWINGS

The invention will now be described with reference to the drawings wherein.

DETAILED DESCRIPTION

In the figures, identical reference signs denote identical features and functions.

Figure 1:
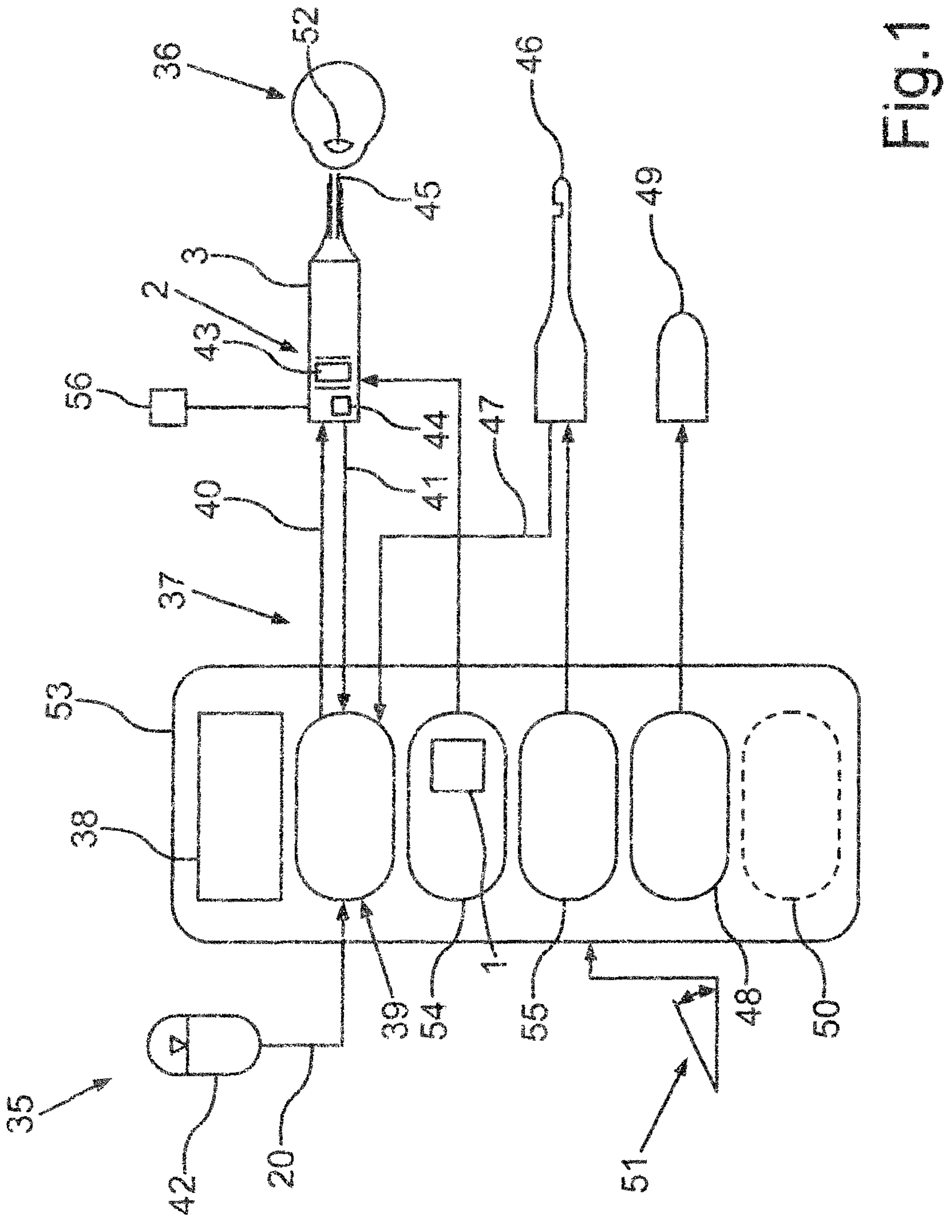
FIG. 1 shows a schematic illustration of an embodiment of an ophthalmic surgical system with one embodiment of an ophthalmic surgical apparatus including an ophthalmic surgical handpiece connected to a controller of the ophthalmic surgical apparatus.

FIG. 1 shows a schematic illustration of an ophthalmic microsurgical system or an ophthalmic surgical system 35 for phaco-surgery on a human eye 36. The illustration in accordance with FIG. 1 shows some components of the system 35 symbolically for the simplified explanation of the basic general functioning of the system 35.

The ophthalmic surgical system 35 includes a console 53 as an equipment unit that may be a trolley, for example, or the like. Preferably, an operating unit 38 is arranged in or on the console 53. By way of example, this operating unit 38 may include a user interface, an input unit such as a keyboard or the like and a display unit such as a monitor or display. Furthermore, a fluidic system 39 including a pumping apparatus and a control device for controlling the pump and connected components is preferably arranged in the console 53. The fluidic system 39 includes an irrigation apparatus with an irrigation line 40 and an aspiration apparatus with an aspiration line 41. The irrigation apparatus includes a container 42 for rinsing liquid, for example a BSS solution, which is a fluid for irrigation and which is guided to a phaco-handpiece. The phaco-handpiece is an ophthalmic surgical handpiece 3. In particular, it is a constituent part of the ophthalmic surgical system 35. The aspiration line 41 is also connected to the ophthalmic surgical handpiece 3.

Moreover, the console 53 includes an ultrasonic unit 54 in particular, the latter being configured to excite an oscillation of piezoelectric elements 43 in the ophthalmic surgical handpiece 3, via which a hollow needle 45, as treatment needle of the ophthalmic surgical handpiece 3, is excited to oscillate. The piezoelectric elements 43 form a piezo-based drive unit 2. In the present case, the ultrasonic unit 54 includes at least one control unit 1 with at least an AC voltage generator, a generator control unit and a voltage sensor (not depicted here).

Further, the console 53 includes a control unit 55, in particular. The control unit 55 can also be configured to control a vitrectomy handpiece 46 which, in particular, may be a constituent part of the ophthalmic surgical system 35. By preference, the vitrectomy handpiece 46 is also connected to the fluidic system 39, in particular by an aspiration line 47. Moreover, provision can be made for a further instrument control unit 48, the latter controlling a preferably available further surgical instrument 49, for example for diathermy. Moreover, the system 35 and, in particular, the console 53 may include further modules and control units and systems, which are represented symbolically by the unit 50. This also includes further internal units, and also peripheral devices. Moreover, the ophthalmic surgical system 35 preferably includes a foot control panel 51, which is connected to the console 53, in particular to communication devices and control units of the console 53.

Moreover, FIG. 1 schematically shows a natural crystalline lens 52 in the eye 36. This crystalline lens 52 can be removed by the ophthalmic surgical system 35, in particular by phacoemulsification.

In an alternative embodiment, provision can be made for the ophthalmic surgical system 35 to include a tank 44 (FIG. 1) which is separate from the container 42. In such an embodiment, the cooling fluid that is provided to cool the incision is provided separately from the irrigation apparatus and separately from the container 42. The tank 44 can be arranged separately from the handpiece 3 and, for example, can be connected to the handpiece 3 via a line, such as a tube connection.

In a further embodiment, provision can be made for the separate tank 44 to be arranged in the handpiece 3. It can be arranged in the handpiece 3 in a non-destructively non-detachable or non-destructively detachable fashion. Provision can also be made for a first separate tank 44 to be arranged in the handpiece 3 and for a further separate tank 56 to be arranged externally to the handpiece 3. This further separate tank 56 external to the handpiece 3 can be connected in fluid-guiding fashion to the first separate tank 44 arranged in the handpiece 3.

Figure 1A:
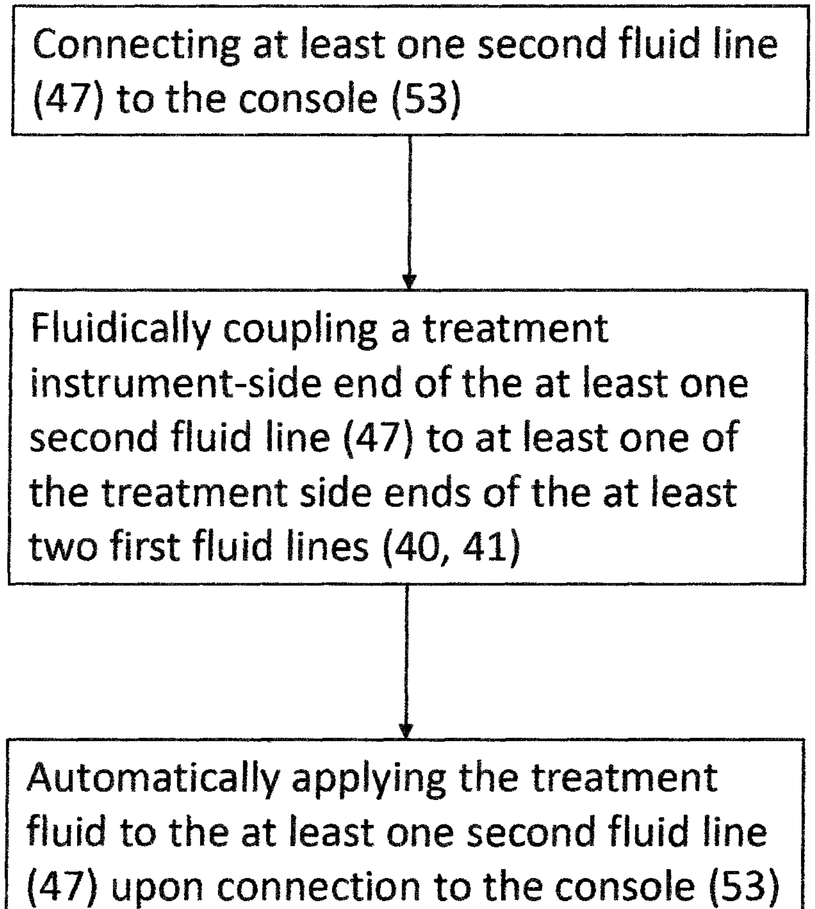
FIG. 1A is a flowchart showing an embodiment of the disclosure.
Figure 2:
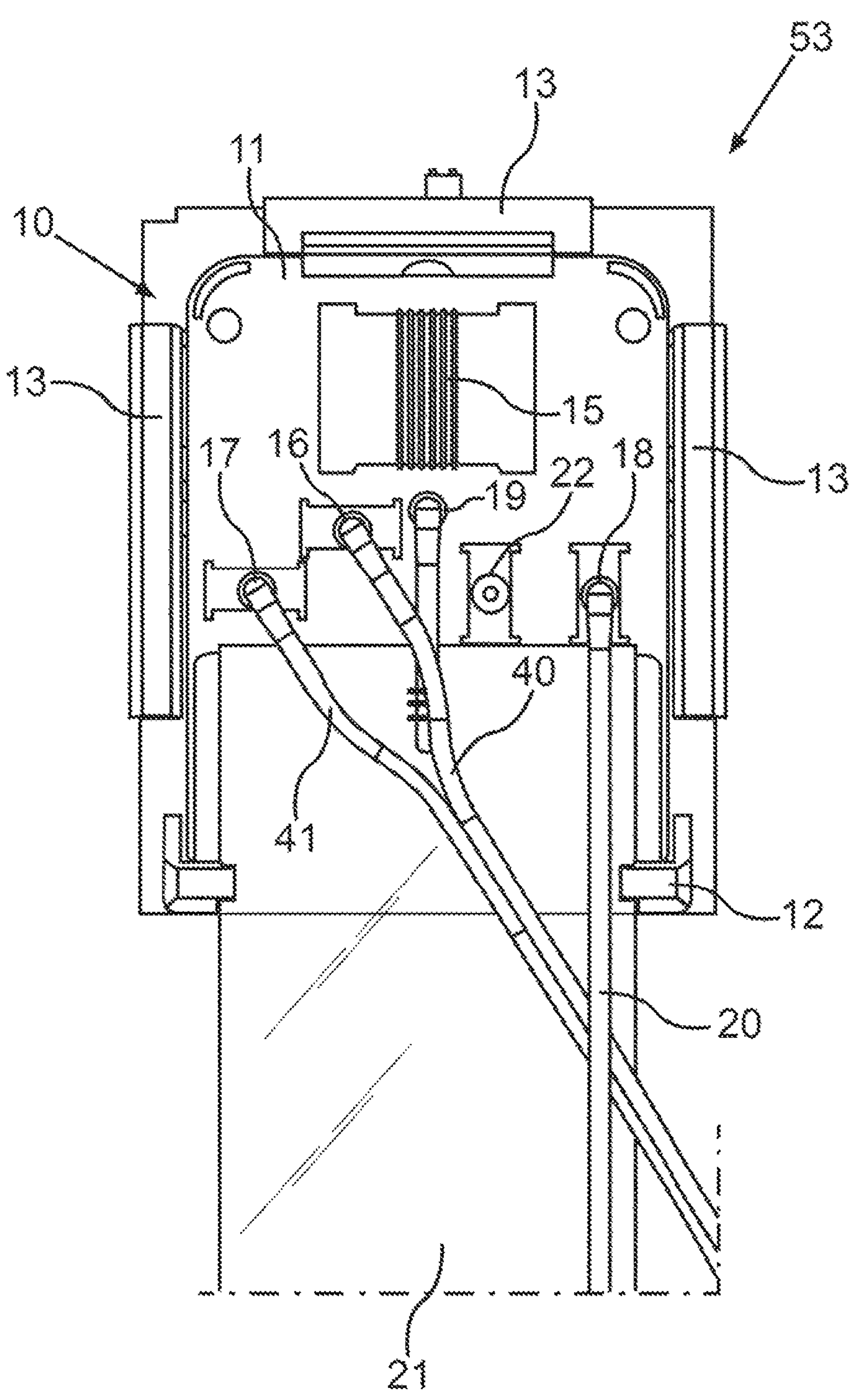
FIG. 2 shows a schematic plan view of a front side of a console of the ophthalmic surgical system according to FIG. 1, in the case of which a cartridge is arranged in a cartridge receiving region of the console.
Figure 3:
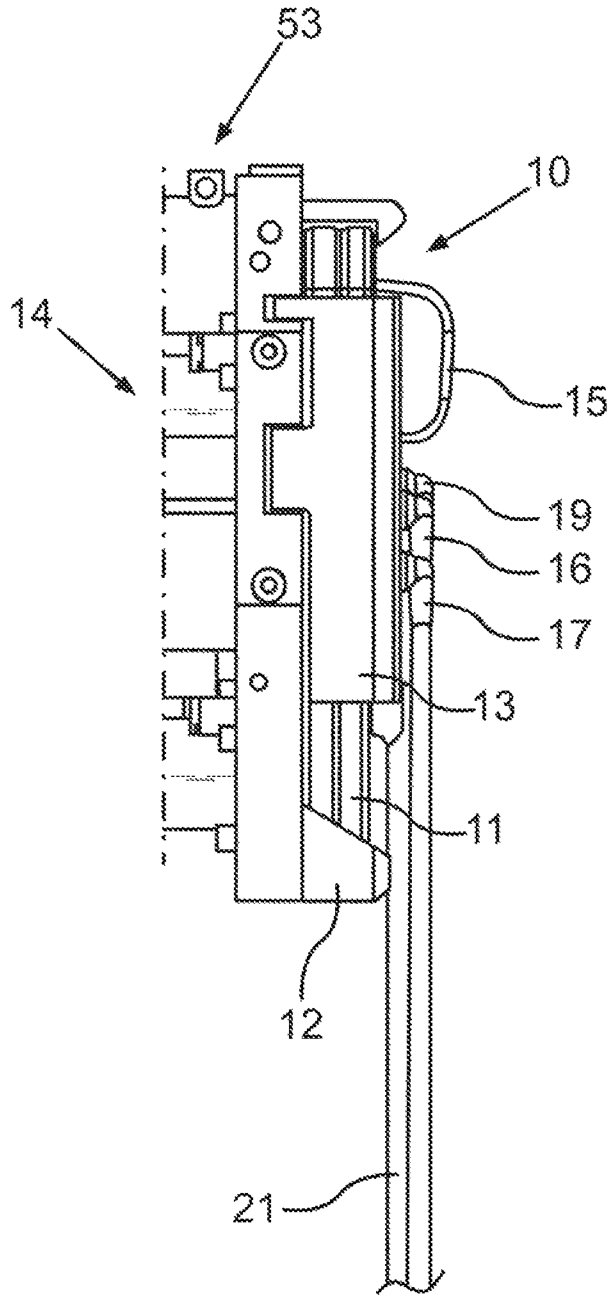
FIG. 3 shows a schematic side view of the console according to FIG. 2; and, FIG. 4 shows a schematic perspective view of the console according to FIG. 2.
Figure 4:
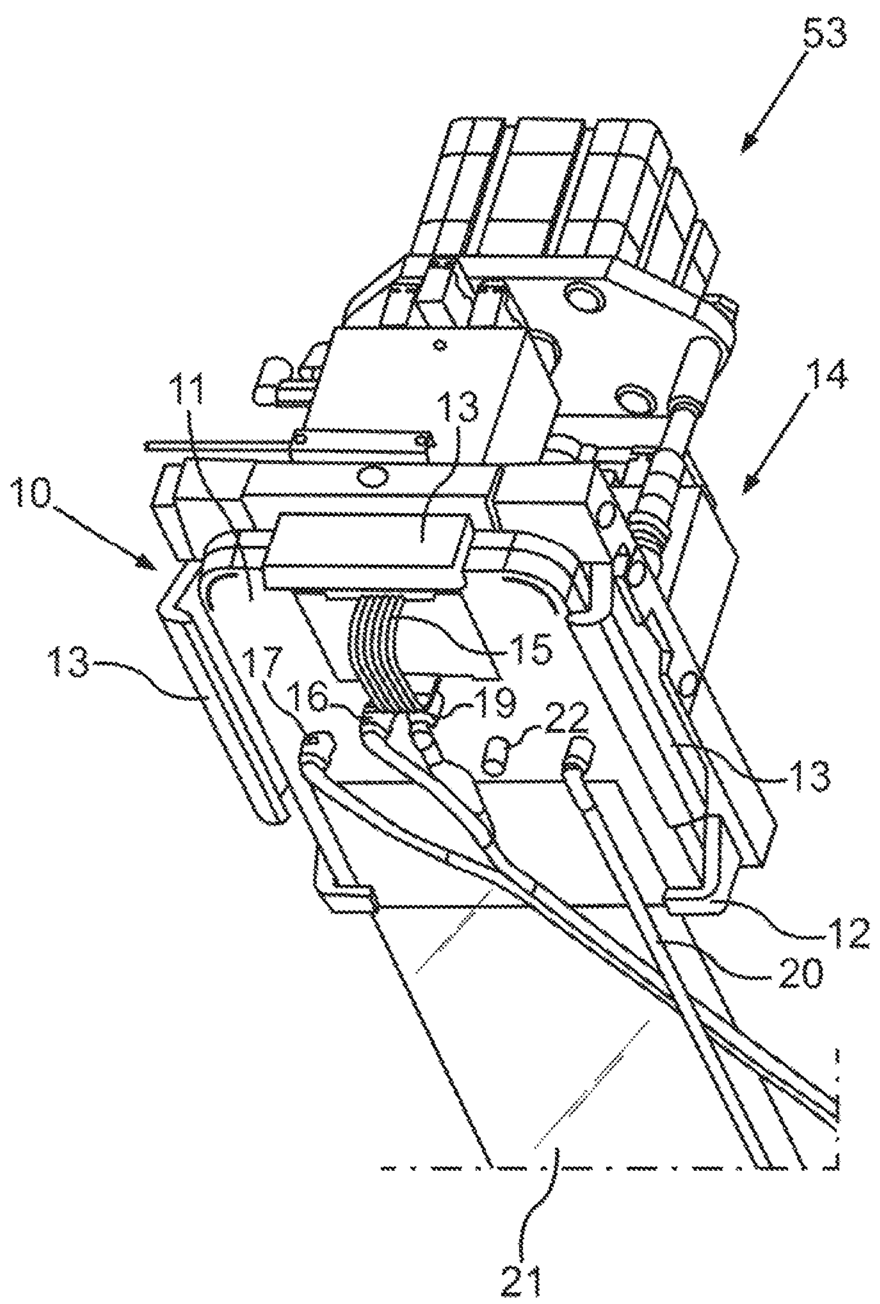

FIG. 1A is a flowchart wherein the at least one second fluid line is connected to the console, a treatment-side in which the second aspiration line 47 couples the console to the at least one medical treatment instrument 3. FIGS. 2 to 4 show the console 53 in different views to render the details more apparent. FIG. 2 shows the console 53 in a plan view of a front side, whereas FIG. 3 shows the console 53 in a schematic side view and FIG. 4 shows the console 53 in a schematic perspective view.

It is evident from FIG. 2 that the console includes a cartridge receiving region 10, in which a cartridge 11 is arranged. The cartridge receiving region 10 is delimited in a lower region by a cartridge support 12, which holds the cartridge 11 in the vertical direction on account of gravity. On the sides of the cartridge receiving region 10 and on an upper side, the console 53 includes retaining brackets 13 which engage over the cartridge 11 in the state where the latter is inserted in the cartridge receiving region 10, as depicted in FIGS. 2 to 4, and hence affix the cartridge in this position on the console 53.

In the present case, the cartridge 11 includes all elements of the console 53 which are in contact with the irrigation fluid and the aspiration fluid. The cartridge 11 is configured as an interchangeable single use part in order thus to be able to reestablish the sterility of the console 53 with little outlay for a subsequent treatment.

To this end, the cartridge 11 includes a pumping apparatus with fluid pumps, although these are not depicted in the figures. The cartridge 11 also includes valves (not illustrated) of a valve apparatus, via which the conveyance of the treatment fluid, irrigation fluid and aspiration fluid can be controlled. To this end, control and actuation elements 14 are provided console side opposite the cartridge 11 in the cartridge receiving region 10 and are in contact with the cartridge 11 in the state where the cartridge 11 is inserted in the cartridge receiving region 10, in order to be able to establish the intended functionality with regards to the fluidic system 39 via the cartridge 11.

In the present case, provision is made for the cartridge 11 to be inserted manually into the cartridge receiving region 10 and also be removed again manually from the latter after use. To this end, the cartridge 11 includes a handle 15.

The cartridge 11 also includes an irrigation connector 16 and an aspiration connector 17, which are fluidically connected to the respective irrigation line 40 and the aspiration line 41. The irrigation line 40 and the aspiration line 41 are connected to the ophthalmic surgical handpiece 3. Moreover, the cartridge 11 includes an irrigation connector 18 which is fluidically coupled to the container 42 via an irrigation line 20. The irrigation liquid is supplied to the cartridge 11 from the container 42 via the irrigation line 20. The cartridge 11 also includes an aspiration connector 19, to which a collecting container 21 is connected. The aspiration fluid aspirated from the handpiece 3 via the aspiration line 41 or the aspiration liquid is guided via the aspiration connector 19 to the collecting container 21 and is collected or stored there. The collecting container 21 can be interchangeable.

The cartridge 11 includes, at least in part, the pumping apparatus and the valve apparatus, which are covered by the console-side control and actuation elements 14 in order to be able to appropriately convey the fluid flows through the fluid lines. Thus, the cartridge 11 is used to supply the irrigation fluid, which is supplied via the irrigation connector 18 of the cartridge 11, to the handpiece 3 via the irrigation connector 16 and the irrigation line 40. Conversely, aspiration fluid received by the handpiece 3 is supplied to the cartridge 11 via the aspiration line 41 and the aspiration connector 17 and, from the cartridge, supplied to the collecting container 21 via the aspiration connector 19. The desired conveying effect is achieved by the pumping apparatus in conjunction with the valve apparatus.

FIGS. 2 to 4 also depict that the cartridge 11 includes a second aspiration connector 22. As evident from FIG. 1, the latter serves to connect the second aspiration line 47 of the vitrectomy handpiece 46. During the intended use, the cartridge 11 is therefore used to discharge aspiration fluid not only via the handpiece 3 but also via the vitrectomy handpiece 46.

To operate the ophthalmic surgical system 35, provision is made for handpiece-side ends of the aspiration line 41 and irrigation line 40, which form first fluid lines in the present case, to be fluidically coupled to one another. The pumping apparatus of the cartridge 11 is used to convey the irrigation fluid from the container 42 to the collecting container 21 of the ophthalmic surgical system 35 through the irrigation line 40 and the aspiration line 41.

Furthermore, the second aspiration line 47 with the vitrectomy handpiece 46 is connected console side to the cartridge 11 of the console 53, which is fluidically coupled to the vitrectomy handpiece 46. A vitrectomy handpiece-side end of the aspiration line 47 is fluidically coupled to the handpiece-side end of the irrigation line 40 via fluidic system 39. The console-side pumping apparatus is used to convey the treatment fluid or irrigation fluid through the second aspiration line 47 by way of suitably controlling the valve apparatus. As a result, it is possible to rinse or prime all fluid lines 40, 41, 47. This is preferably implemented in a single method step such that no further rinsing procedure need to be carried out for the purpose of performing the surgical procedure.

In the present case, provision is made for the console 53 to detect the connection of the second aspiration line 47 by way of the cartridge 11, in particular by way of the sensors provided there. Subsequently, the irrigation fluid is automatically applied to the second aspiration line 47. Thus, no separate action needs to be carried out by the user anymore.

In an alternative, or cumulatively, provision can be made for the irrigation fluid to be applied to the second aspiration line 47 only once the vitrectomy handpiece 46 is put into operation during a surgical procedure, during which the handpiece 3 is already in use. To this end, provision can be made for the possibility of realizing an individual control via the valve apparatus of the console 53 in conjunction with the cartridge 11.

Moreover, provision is presently made for respective fluid resistances in relation to the conveyance of the irrigation fluid or aspiration fluid to be ascertained for the fluid lines 40, 41, 47 via sensors provided at least in part on the console side, in particular on the cartridge side. On the basis thereof, the control unit 55 or the ultrasonic unit 54 determines the respective connected medical treatment instrument, in this case the handpiece 3 or the vitrectomy handpiece 46. On the basis thereof, operational parameters for the handpieces 3, 46 are set automatically. Thus, the user of the ophthalmic surgical system 35 need not adjust any separate settings in this respect. As a result, reliability and safety can be further improved.

In particular, a respective handpiece 3, 46 can be identified in this way. Naturally, identification of the handpiece by way of RFID or the like may also be provided cumulatively or in an alternative. The required operational parameters can be retrievably stored in a memory unit of the console 53. However, provision can also be made for the console 53 to retrieve the appropriate operational parameters for the respectively identified handpiece 3, 46 via a communications link to a central database, and adjust the appropriate settings.

Thus, the disclosure makes it possible to rinse or prime handpieces, preferably before a surgical procedure. Moreover, it is naturally also possible to individually rinse or prime a handpiece newly added during a surgical procedure. However, due consideration should be given to the fact that priming may interrupt the surgical procedure under certain circumstances because the fluidic supply for the already operational handpiece might not be able to be maintained during priming or rinsing.

By preference, rinsing or priming also includes the cartridge 11 of the console 53.

Moreover, if more than a single handpiece is connected to the console 53 or cartridge 11, provision can naturally be made for the connected handpieces to be successively rinsed or primed by way of a suitable control, without the user having to perform further actions.

In the present case, the operational parameter may for example refer to a fluidic diameter, which may for example range from approximately 19 gauge to approximately 27 gauge, that is, have a range for an internal diameter from approximately 1.1 millimeters to approximately 0.4 millimeters. The fluid resistance is preferably stored in the form of data in a table. The internal diameter of the fluid lines 40, 41, 47 can be calculated on the basis of the ascertained fluid resistance, and the operational parameters can be set appropriately therefor.

Overall, the disclosure makes it possible to further improve the use of the ophthalmic surgical system.

The embodiments serve exclusively for explaining the disclosure and do not restrict it.

It is understood that the foregoing description is that of the preferred embodiments of the invention and that various changes and modifications may be made thereto without departing from the spirit and scope of the invention as defined in the appended claims.

LIST OF REFERENCE SIGNS

1 Control unit
2 Drive unit
3 Handpiece
10 Cartridge receiving region
11 Cartridge
12 Cartridge support
13 Retaining brackets
14 Actuation elements
15 Handle
16 Irrigation connector
17 Aspiration connector
18 Irrigation connector
19 Aspiration connector
20 Irrigation line
21 Collecting container
22 Aspiration connector
35 Ophthalmic surgical system
38 Operating unit
39 Fluidic system
40 Irrigation line
41 Aspiration line
42 Container
46 Vitrectomy handpiece
47 Aspiration line
53 Console
54 Ultrasonic unit
55 Control unit

The invention claimed is:

1. A method for operating an ophthalmic surgical system, the method comprising:

providing the ophthalmic surgical system, the ophthalmic system comprising:

a console, at least one medical treatment instrument, a treatment fluid source, a treatment fluid, a pumping apparatus, a collecting container, at least two first fluid lines comprising at least one first irrigation line and at least one first aspiration line, and at least one second fluid line for the treatment fluid, detecting that at least one second fluid line has been connected to a console; and, automatically applying a treatment fluid to the at least one second fluid line upon connection to the console, wherein:

treatment instrument-side ends of the at least two first fluid lines are fluidically coupled to one another via a fluidic coupling, wherein the fluidic coupling is made prior to medical treatment of an eye;

the at least two first fluid lines are connected to the console, fluidically couple the console to the at least one medical treatment instrument, and are configured to have the treatment fluid conveyed therethrough from the treatment fluid source to the collecting container via the pumping apparatus;

the at least one second fluid line is configured to be connected to the console for fluidically coupling the console to the at least one medical treatment instrument or a further medical treatment instrument;

a treatment instrument-side end of the at least one second fluid line is fluidically coupled to at least one of the treatment instrument-side ends of the at least two first fluid lines;

the at least one second fluid line is configured to have the treatment fluid conveyed therethrough via the pumping apparatus; and said detecting that the at least one second fluid line has been connected to the console is performed during a surgical procedure.

2. The method of claim 1, wherein said automatically applying the treatment fluid to the at least one second fluid line is performed during use of the at least one medical treatment instrument.

3. The method of claim 1, wherein the at least one second fluid line is a second aspiration line for fluidically coupling the further medical treatment instrument.

4. The method of claim 1, wherein the console is configured to activate the at least two first fluid lines and the at least one second fluid line individually via a valve apparatus.

5. The method of claim 1, wherein, a fluid resistance is ascertained in relation to the conveyance of the treatment fluid through one of the at least two first fluid lines and the at least one second fluid line.

6. The method of claim 5, wherein at least one operational parameter of the ophthalmic surgical system is set on a basis of the ascertained fluid resistance.

7. The method of claim 6, wherein the medical treatment instrument connected to the at least one of the at least two first fluid lines and the at least one second fluid line for which the fluid resistance is ascertained is determined at least on the basis of the ascertained fluid resistance.

8. The method of claim 6, wherein the medical treatment instrument connected to the at least one of the two first fluid lines and the at least one second fluid line is determined at least on the basis of the ascertained fluid resistance, with at least one operational parameter of the determined medical treatment instrument being set on a basis of the determined medical treatment instrument.

9. A method for operating an ophthalmic surgical system, the method comprising:

providing the ophthalmic surgical system, comprising:

a console, at least one medical treatment instrument, a treatment fluid source, a treatment fluid, a pumping apparatus, a collecting container, at least two first fluid lines comprising at least one first irrigation line and at least one first aspiration line, and at least one second fluid line for the treatment fluid, detecting that the at least two first fluid lines and the at least one second fluid line have been connected to the console; and, automatically applying the treatment fluid to the at least two first fluid lines and the at least one second fluid line upon said detecting that the at least two first fluid lines and the at least one second fluid line have been connected to the console, wherein:

treatment instrument-side ends of the at least two first fluid lines are fluidically coupled to one another via a fluidic coupling, wherein the fluidic coupling is made prior to medical treatment of an eye;

the at least two first fluid lines are connected to the console, fluidically couple the console to the at least one medical treatment instrument, and are configured to have the treatment fluid conveyed therethrough from the treatment fluid source to the collecting container via the pumping apparatus;

the at least one second fluid line is configured to be connected to the console for fluidically coupling the console to the at least one medical treatment instrument or a further medical treatment instrument;

a treatment instrument-side end of the at least one second fluid line is fluidically coupled to at least one of the treatment instrument-side ends of the at least two first fluid lines;

the at least one second fluid line is configured to have the treatment fluid conveyed therethrough via the pumping apparatus; and said detecting that the at least one second fluid line has been connected to the console is performed during a surgical procedure.

* * * * *